United States Patent
Kosashvili et al.

(10) Patent No.: US 7,135,022 B2
(45) Date of Patent: Nov. 14, 2006

(54) MAGNETICALLY-ACTUABLE INTRAMEDULLARY DEVICE

(75) Inventors: Yona Kosashvili, Rishon-Lezion (IL); Dror Robinson, Shimshon (IL)

(73) Assignee: Orthogon 2003 Ltd., Ofakim (IL)

( * ) Notice: Subject to any disclaimer, the term of this patent is extended or adjusted under 35 U.S.C. 154(b) by 241 days.

(21) Appl. No.: 10/478,717

(22) PCT Filed: May 22, 2002

(86) PCT No.: PCT/IL02/00401

§ 371 (c)(1),
(2), (4) Date: Nov. 24, 2003

(87) PCT Pub. No.: WO02/094113

PCT Pub. Date: Nov. 28, 2002

(65) Prior Publication Data

US 2004/0138663 A1    Jul. 15, 2004

(30) Foreign Application Priority Data

May 23, 2001 (IL) ........................... 143334
Dec. 18, 2001 (IL) ........................... 147156

(51) Int. Cl.
*A61B 17/56* (2006.01)
*A61B 17/58* (2006.01)
*A61F 2/28* (2006.01)

(52) U.S. Cl. ....................... 606/63; 623/23.47

(58) Field of Classification Search ............... 606/62, 606/86, 87, 95, 63, 60; 623/18.12, 23.45, 623/23.47; 403/43–48, 109.1–109.8
See application file for complete search history.

(56) References Cited

U.S. PATENT DOCUMENTS 3,745,995 A    7/1973 Kraus (Continued)

FOREIGN PATENT DOCUMENTS

WO    WO 95/21580    8/1995

(Continued)

OTHER PUBLICATIONS

A.A. Kazakov and N.V. Kudrevatykh, "Temperture dependence of single-ion anisotropy and magnetostriction coefficients of rare earth ferromagnets in terms of quantum theory", Jan. 29, 1993, Journal of Alloys and Compounds, vol. 191 Issue 1, pp. 67-70.*

(Continued)

*Primary Examiner*—Corrine McDermott
*Assistant Examiner*—Thomas J. Sweet
(74) *Attorney, Agent, or Firm*—Nixon & Vanderhye

(57) ABSTRACT

The present invention provides a two-part telescopic intramedullary orthopedic device comprising a first section inserted into the medullary cavity of one of the fractured or severed bone ends, and secured thereto, and a second section inserted into the medullary cavity of the other fractured or severed bone end and secured thereto, wherein the first section is telescoped within the internal space of the second section, and wherein one of the sections comprises a ferromagnetic material and the other section is either constructed entirely of a non-magnetic material or comprises a ferromagnetic material, wherein the ferromagnetic section(s) are actuable by an external axially directed magnetic field, such that one section may be caused to move axially (either bidirectional or essentially unidirectional) in relation to the other section. In addition, the invention encompasses a method for changing bone length as well as a method for enhancing bone fracture healing.

55 Claims, 3 Drawing Sheets

U.S. PATENT DOCUMENTS

| | | | | |
|---|---|---|---|---|
| 3,915,151 A | * | 10/1975 | Kraus | 600/13 |
| 5,263,955 A | * | 11/1993 | Baumgart et al. | 606/63 |
| 5,350,379 A | * | 9/1994 | Spievack | 606/63 |
| 5,356,411 A | * | 10/1994 | Spievack | 606/63 |
| 5,505,733 A | * | 4/1996 | Justin et al. | 606/63 |
| 5,536,269 A | * | 7/1996 | Spievack | 606/63 |
| 5,626,579 A | | 5/1997 | Muschler et al. | |
| 5,704,938 A | | 1/1998 | Staehlin et al. | |
| 5,704,939 A | | 1/1998 | Justin | |
| 5,984,856 A | * | 11/1999 | Love | 600/15 |
| 6,019,761 A | * | 2/2000 | Gustilo | 606/62 |
| 6,022,349 A | | 2/2000 | McLeod et al. | |
| 6,032,677 A | | 3/2000 | Blechman et al. | |
| 6,200,317 B1 | * | 3/2001 | Aalsma et al. | 606/62 |
| 6,383,185 B1 | * | 5/2002 | Baumgart | 606/63 |
| 6,796,984 B1 | * | 9/2004 | Soubeiran | 606/61 |
| 6,849,076 B1 | * | 2/2005 | Blunn et al. | 606/105 |
| 2004/0030395 A1 | * | 2/2004 | Blunn et al. | 623/18.12 |

FOREIGN PATENT DOCUMENTS

WO    WO 99/51160    10/1999

OTHER PUBLICATIONS

R. Skomski, "Curie temperature and density of states of quasi-weak ferromagnets", Feb. 1995, Journal of Magnetism and Magnetic Materials, vol. 140-144 Part 3, pp. 2003-2004.*

Kenwright et al., "Controlled Mechanical Stimulation in the Treatment of Tibial Fractures," Clinical Orthopedic and Related Research, No. 241, Apr. 1989, pp. 36-47.

* cited by examiner

MAGNETICALLY-ACTUABLE INTRAMEDULLARY DEVICE

This application is the US national phase of international application PCT/IL02/00401, filed in English on 22 May 2002, which designated the US. PCT/IL02/00401 claims priority to IL Application No. 143334, filed 23 May 2001 and IL Application No. 147156, filed 18 Dec. 2001. The entire contents of these applications are incorporated herein by reference.

FIELD OF THE INVENTION

The present invention relates generally to a magnetically-actuated orthopedic implant for use in promoting the healing of bone fractures and in manipulating bone length. More particularly, the present invention relates to an intramedullary device capable of changing its length in a cyclic manner under the influence of an electromagnetic field, said device being particularly suitable for the treatment of cases in which there is non-union of the fractured bone ends, as well as for the primary treatment of long bone fractures.

BACKGROUND OF THE INVENTION

The use of implant devices in the management of many orthopedic conditions is well known in the art. In some cases, the use of such internally-fitted devices may be the only effective way of stabilizing fractured bones. However, this approach suffers from the drawback that, once in place, the length and/or position of the implant cannot be physically manipulated without further surgical intervention. This is a particular drawback when implants are used in order to achieve one or both of the following clinical goals:
  a) increase or decrease in bone length, and
  b) accelerated healing of bone fractures.

It is known in orthopedic surgery to sever a bone, such as a tibia or femur, in order to increase its overall length and thereby correct a skeletal or other defect. One common procedure for this purpose makes use of a special nail that is implanted in an intramedullary fashion into the bone to be lengthened. A longitudinally-adjustable frame external to the appendage containing the bone to be lengthened is secured at one end of the bone and it is attached at its other end to the nail as well as to the other end of the bone.

The bone is then osteotomized by the surgeon and the adjustable frame is periodically lengthened, thereby causing the bone, while the break therein is knitting, to assume a desired overall length. The implant is then embedded in the lengthened bone.

As pointed out in U.S. Pat. No. 5,704,938 to Staehlin et al. (1998) the external frame fixation system used in this known bone lengthening procedure is difficult to securely locate on the patient and not only gives rise to discomfort, but it also presents an unattractive appearance. Moreover, pins anchored in the bone and protruding through the skin to join the frame increases the risk of infection and nerve injury, either immediate or delayed, during the lengthening procedure.

To overcome these drawbacks, Staehlin provides a bone-lengthening device which is wholly implantable, except for a tube extending from the device and passing through the skin to supply a hydraulic fluid to the implant which is hydraulically adjustable in length.

Staehlin's two-part implant is mechanically complicated, for it includes a drive bolt located in one part that extends into the other part, which bolt, when rotated by a drive mechanism is activated by a hydraulically-operated plunger making it necessary to supply through a tube leading into the implant a pressurized hydraulic fluid.

In their least complicated forms, bone fractures may be treated by simple immobilization of the relevant body part. In many case, particularly when the fracture occurs in a long bone, this type of management may be sufficient to permit the body's natural processes to completely close the fracture and to lead to complete healing of the affected bone. In other cases, the distance between the mating surfaces of a fractured bone may be so great as to result in non-union of the fracture. Clinically, non-union of fractures is often defined as failure of the fracture fragments to unite after 8 months. Typically, such a situation can arise from excessive movement at the fracture site, soft tissue interposition, infection, or trauma. In such cases, the normal process of calcification fails to take place and the fracture gap remains occupied by fibrocartilage and/or fibrous tissue. Ingrowth of new blood vessels cannot take place, and normal healing will be prevented.

It has been found that application of cyclic compressive forces to the fracture (in imitation of the normal weight bearing forces) accelerates this process by up to one third of the normal healing time. This effect will be discussed in more detail hereinbelow.

Currently, long bone fractures are preferably treated by the use of intramedullary nails or rods. The stability of these implant devices, and the reduced soft tissue damage caused thereby, render this approach preferable over open reduction techniques. However, although these implants permit weight bearing forces to be exerted thereon, they often isolate the fracture from compression forces due to the presence of locking screws, whose primary purpose is to prevent rotation. Also, as a result of the fixed distance between the fracture ends imposed on the fracture by virtue of their rigid structure, intramedullary nails can actually cause cases of fracture of non-union. Various studies have estimated that the incidence of non-unions that result directly from the use of intramedullary nails may reach up to 5% of all fracture cases treated with these devices.

Various other techniques for managing non-union fractures have been used and reported in the art. For example, different forms of electrical stimulation have been investigated. These basic studies have in turn led to a number of proposals for promoting the healing of bone fractures, including invasive treatments involving the use of implanted electrodes as well as non-invasive techniques utilizing electrostatic and electromagnetic fields.

U.S. Pat. No. 3,745,995, for example, describes metal splints that are affixed to fractured bone by means of screws. The device further comprises pickup coils having terminals connected both to said splints and to electrodes invasively inserted into the bone. A coil surrounding the limb having the fracture induces in the pickup coils an alternating current signal. In this way, the electrical signals are transmitted to the fracture ends.

In another approach, the use of mechanical stimuli to promote healing of non-union fractures has been described. For example, in one study [J. Kenwright & A. E. Goodship, Clin. Ortho. & Rel. Res. (1989) 241: 36–47] the effects of mechanical stimulation on midshaft tibial breaks were investigated in experimental animals. The applied stimulation had frequencies approximating that of the walking frequency of the animal used. Cyclic loading of the fracture region for 17 minutes per day was used. Although useful results were obtained in these experimental studies, it was found that it was critical to accurately control the displacements of the fractured bones, as high displacements were noted to lead to mechanical failure of the wound healing process.

U.S. Pat. No. 6,022,349 describes a method and system for treating bone fractures and osteoporosis that is based on the mechanical stimulation described in the aforementioned study by Kenwright and Goodship. However, it would appear that the apparatus described therein is not capable of producing the controlled, axially-directed oscillatory movements that imitate normal force-loading on the affected limb (e.g. the cyclic compression that occurs during walking), that have been shown to be useful in accelerating fracture healing.

U.S. Pat. No. 6,032,677 discloses a method and apparatus for stimulating the healing of medical implants, particularly those used in dental surgery. The apparatus described therein uses an internally-placed permanent magnet and externally applied electromagnetic field to cause oscillation of the implant within a tooth socket or medullary cavity of a fractured bone.

It is a purpose of the present invention to provide a reliable implant device and method for the alteration of bone length.

It is another purpose of the present invention to provide the aforementioned implant device in a form suitable for the management of bone fractures, particularly long bone fractures, and more particularly, cases of non-union of said long bone fractures.

It is a further aim of the present invention to provide a device for managing bone fractures that will act to prevent the occurrence of fracture non-union, by permitting movement of the fractured bone ends towards each other.

Yet a further purpose of the invention is to provide a device and method for managing fractures that will reduce the time required for complete healing.

It is another purpose of the invention to provide a device and method that may be applied during the initial stages of the treatment of bone fractures.

It is a further purpose of the invention to provide a method for managing non-union fractures or for elongating or shortening bones that does not require the complete immobilization of the patient, or the use of uncomfortable and unaesthetic externally-placed devices such as external fixation frames.

It is yet another purpose of the present invention to provide a device for the management of non-union fractures that overcomes the problems and disadvantages of prior art devices.

It is yet another purpose of the present invention to provide a device for elongating or shortening bones that overcomes the problems and disadvantages of prior art devices.

Further objects and advantages of the present invention will become apparent as the description proceeds.

SUMMARY OF THE INVENTION

The present invention is primarily directed to a two-part telescopic intramedullary orthopedic device capable of connecting two adjacent fractured or severed bone ends, characterized in that said device comprises
  a first section inserted into the medullary cavity of one of the fractured or severed bone ends, and secured thereto, and
  a second section inserted into the medullary cavity of the other fractured or severed bone end and secured thereto,
  wherein said second section comprises an internal space communicating with an external opening, and wherein said first section is more or less telescoped within said internal space of said second section, and
  wherein one of said sections comprises a ferromagnetic material and the other section is either constructed entirely of a non-magnetic material or comprises a ferromagnetic material, wherein the ferromagnetic section(s) are actuable by an external magnetic field, such that one section may be caused to move axially in relation to the other section, and wherein said axial movement may be either bidirectional or essentially unidirectional.

The "move axially" and "axial movement" as used herein refer to movement of the ferromagnetic section or sections of the device in a direction parallel to the long axis thereof. Said axial movement may occur either bidirectionally (that is, in an oscillatory manner) or essentially unidirectionally, as will be described in the following sections.

It has now been unexpectedly found that the above-defined two-part telescopic device may be used both to promote the accelerated healing of bone fractures, as well as to change bone length. It is to be emphasized that the accelerated healing effect may be obtained either in conjunction with bone-length alteration, or as a separate effect, in the absence of changes in bone length. It was further found that the accelerated healing effect occurs when the axial movement of the telescopic device is bidirectional (that is, oscillatory), while bone lengthening or shortening is obtained when said axial movement is unidirectional. It has further been found that by alternating the mode of axial movement between unidirectional and bidirectional, it is possible to promote healing of the severed bone fragments in addition to inducing changes in the final length of the severed bone.

The term "severed" bone ends, as used hereinabove and throughout this application is used to indicate the situation where the bone to be treated was intentionally severed into two portions by a surgeon as part of a procedure for changing the length of said bone. The term "fractured" bone ends, however, is used to indicate the more common situation, wherein a patient presents with a bone fracture that was caused by means other than planned surgical intervention.

Thus in one aspect, the present invention is directed to a device as disclosed hereinabove, wherein the axial movement of one section of said device in relation to the other section is essentially unidirectional such that the first section of said device may be caused to shift progressively in one direction with respect to the second section, thereby changing the separation between the fractured or severed bone sections.

It is to be noted that the term "essentially unidirectional", as used hereinabove, is employed to indicate that although the main mode of axial movement is in one direction only, the device of the invention will also permit low-amplitude bidirectional, oscillatory, movement for the purposes of promoting accelerated bone healing.

In one embodiment of the device, the direction of the essentially unidirectional axial movement is such that the relative movement of the two sections of said device causes an increase in the length of the bone.

In another embodiment of the device of the invention, the direction of the essentially unidirectional axial movement is such that the relative movement of the two sections of said device causes a decrease in the length of the bone.

In one preferred embodiment of the invention, the ferromagnetic material used in the construction of the section(s)

comprising such material is a hard ferromagnetic material. Although any suitable hard ferromagnetic material may be used, this is preferably either Alnico or ferrite.

In one preferred embodiment of the device of the invention, the non-magnetic section (if used) is a synthetic plastic material. In another preferred embodiment, the non-magnetic material is titanium.

In one preferred arrangement of the device, the first section of said device is formed by a core of ferromagnetic material, and the second implant section is formed by a tubular socket into which the first section is telescoped.

In one particularly preferred embodiment of the device of the invention, the first section has a non-circular cross section and the internal space of the second section has a corresponding cross section whereby said first section cannot be rotated within said second section.

In one preferred embodiment of the device, telescopic advancement of the first section within the second section by incremental steps is achieved by a series of annular grooves formed along the first section, said grooves defining ratchet teeth that are detented by a pawl mounted on the second section. Preferably, said pawl is a flat spring having a tongue extending into a groove in the series thereof. In another embodiment, a pair of pawls is mounted on opposite sides of the second section. In a particularly preferred embodiment, the aforementioned grooves have a triangular cross section and a groove height with permits the first section ratcheted by the pawl to vibrate.

The device of the present invention may also be constructed such the second implant section includes a reservoir loaded with a flowable healing agent and provided with an orifice from which is emitted a charge of the agent each time the first implant section is advanced an incremental step. This embodiment of the device may further comprise means to subject the agent in the reservoir to a pressure pulse each time the first implant section is advanced to force the agent out of the orifice. Many different healing agents may be used in conjunction with the device, including but not limited to, growth factors which promotes the bone healing process and antibiotics.

In another preferred embodiment, the first section of the device of the invention has a square cross section and the second section which is channel-shaped includes parallel sidewalls banking a cross section area matching the cross section of the first section whereby the first section can be telescopically received in the second section. In an even more preferred embodiment of the device, the first section has a top wall that is notched to define ratchet teeth that are detented by a pawl mounted on the second section whereby the first section can be incrementally advanced beyond the second section.

The present invention is also directed to an orthopedic implant assembly adapted to manipulate the length of a skeletal bone to attain a predetermined length in a procedure in which a canal may be reamed through the bone to accommodate an implant and the bone severed to define complementary bone sections each having a cavity therein to receive a respective section of the implant, said assembly comprising:
  A. a two-part telescopic device, as disclosed hereinabove, and
  B. means external to said device to apply magnetic forces thereto to cause the one or more ferromagnetic sections of said device to shift progressively in one direction with respect to the other section of said device to change the separation therebetween until the severed bone attains said predetermined length.

In one preferred embodiment of the aforementioned assembly, the magnetic forces are constituted by successive impulses each of which causes the first section to advance an incremental step. In a more preferred embodiment of this aspect of the invention, the impulses of magnetic force are produced by applying direct current power pulses to a magnetic field coil adjacent to the bone whose length is to be changed.

In one preferred arrangement of the aforementioned assembly, the bone to be manipulated is embedded in a body appendage and the field coil surrounds the appendage.

The present invention also provides an assembly as disclosed hereinabove that further comprises means for applying an alternating magnetic force to the device after the first section of said device has been incrementally advanced to cause said first section to vibrate to promote the healing process. In one preferred embodiment, the alternating magnetic force is produced by a field coil adjacent to the device to which an alternating voltage is applied. In a particularly preferred embodiment said alternating voltage is generated by an oscillator whose frequency is such as to promote the healing process.

In another aspect, the present invention is directed to a method of lengthening or shortening a skeletal bone to attain a predetermined length comprising the steps of:
  A. reaming the marrow of the bone to be lengthened or shortened to create a canal to accommodate a two-part telescopic intramedullary orthopedic device having a first section more or less telescoped within a second section, wherein one of said sections comprises a ferromagnetic material and the other section is either constructed of a non-magnetic material or comprises a ferromagnetic material;
  B. severing the bone to define complementary bone sections, each having a cavity therein;
  C. inserting the first section of the device into the cavity in one section of the bone and securing it thereto;
  D. inserting the second section of the device into the cavity of the other bone section and securing it thereto, whereby the degree to which the bone sections are separated and the severed bone is lengthened or shortened depends on the extent to which the first section projects beyond the second section; and
  E. applying successive magnetic force impulses to the first section to cause it to advance an incremental step per impulse until the severed bone has attained said predetermined length.

In addition to the use of the aforementioned magnetic force impulses, the method also provides the use of ratchet and/or spring components within the telescopic device to cause the first section of the device to advance an incremental step.

In one embodiment of the above-disclosed method, successive incremental steps in the advance of the first section are separated by time intervals of sufficient duration to permit effective healing of the severed bone. Preferably, the duration of each of said time intervals is at least one full day.

In another preferred embodiment, the method further comprises the step of monitoring the change of length of the implant by use of an imaging technique. In one preferred embodiment, the imaging technique is ultrasonic imaging. In another preferred embodiment, the imaging technique is based on the use of a magnetic sensor.

In a preferred embodiment of the method of the invention, the parameters of the magnetic force lie in the range of 100 to 1000 newtons. In another preferred embodiment of the method, the implant is extended in increments of 0.1 to 1 mm per day. Preferably, 1–6 incremental steps per day are used in order to achieve the desired change in length. More preferably, 4 incremental steps are used each day, each step representing a change in length of 0.1 mm.

The present invention also encompasses a two-part telescopic device, as disclosed hereinabove, wherein the axial movement of one section of the device in relation to the other section is essentially bidirectional such that the ferromagnetic section(s) may be caused to oscillate axially, thereby causing axial oscillatory motion of the fractured or severed bone section(s) to which the device is attached, wherein the axial movement in one direction is caused by the magnetic forces induced by an external magnetic field on the ferromagnetic section(s), and wherein the axial movement in the opposite direction is caused either by magnetic forces having a reversed polarity or by mechanical means.

This aspect of the invention is thus directed to a two-part telescopic device for promoting the healing of bone fractures, comprising
- a first section inserted into the medullary cavity of one of the fractured bone ends and secured thereto, and
- a second section inserted into the medullary cavity of the other fractured bone end and secured thereto,
- wherein said second section comprises an internal space communicating with an external opening, and wherein said first section is more or less telescoped within said internal space of said second section, and
- wherein at least one of said sections comprises a ferromagnetic material that is actuable by an external magnetic field, such that the ferromagnetic section(s) may be caused to oscillate axially,
- wherein the axial movement in one direction is caused by the magnetic forces induced by said magnetic field acting on said ferromagnetic section(s), and wherein the axial movement in the opposite direction is caused either by magnetic forces having a reversed polarity or by mechanical means.

In one preferred embodiment of the device of the invention, the magnetic forces are alternating magnetic forces having forward and reverse directional components, each of the two directions of axial movement being caused by one of said directional components.

In another preferred embodiment of the device of the invention, the magnetic forces are unidirectional magnetic forces, and said device further comprises mechanical means for causing axial movement in a direction opposite to that of said magnetic forces.

In a preferred embodiment, the mechanical means comprise a spring located within the internal space of the second section of the telescopic device, such that said spring is positioned between the base of said internal space and the free end of the first section.

A variety of magnetic and non-magnetic materials may be used in the construction of the device of the present invention. In one preferred embodiment, the ferromagnetic section is at least partially formed by a hard ferromagnetic material. Examples of hard ferromagnetic materials that may be used in the working of the present invention include, but are not limited to, Alnico and ferrite. In a more preferred embodiment of the device of the invention, the section comprising the ferromagnetic material is constructed such that the ferromagnetic material itself is in the form of a 'core' that is completely enclosed by a biocompatible material such as titanium or biocompatible stainless steel alloy such as L-316. This preferred two-layer structure obviates the health hazards associated with direct contact of certain ferromagnetic materials with living tissue.

In the event that one of the two sections of the aforementioned device is entirely non-magnetic, said non-magnetic section may be made of any non-magnetic material possessing the required physical and mechanical properties. These properties include sufficient mechanical strength and rigidity to withstand the cyclical mechanical forces acting on the device, as well as sufficient toughness in order to reduce frictional wear. In addition, the materials need to be biocompatible. In one preferred embodiment, the non-magnetic section is formed of a synthetic plastic material. In another preferred embodiment, the non-magnetic section is formed of titanium.

In another aspect, the apparatus disclosed hereinabove further comprises means for causing the local release of biologically-active agents at the fracture site. Thus, in one preferred embodiment, the second section of the two-part device includes a reservoir loaded with a flowable healing agent and is provided with an orifice from which said agent is emitted. In another preferred embodiment, the apparatus further comprises means for subjecting the agent in the reservoir to a pressure pulse. Many different examples of biologically-active agents that may be used to assist fracture healing are known in the art. Thus, in one preferred embodiment of this aspect of the invention, the healing agent is a growth factor which the ability to promote bone healing. Examples of suitable growth factors Include, but are not limited to: bone morphogenetic protein, transforming growth factor beta, osteogenic growth peptide (OP-1), decalcified bone matrix and parathyroid hormone (PTH).

In another preferred embodiment, the healing agent is an antibiotic agent.

The healing agent may be provided in any suitable physical form that is capable of flowing through the above-mentioned orifice. Suitable physical forms include, but are not limited to, liquids, pastes, creams, granules and beads.

The present invention is also directed to a therapeutic system for promoting the healing of bone fractures comprising a device as disclosed hereinabove, together with means external to said device for applying magnetic forces thereto.

In one preferred embodiment of the therapeutic system of the invention, the means for applying magnetic forces comprises a magnetic field coil situated adjacent to the telescopic device.

In one preferred embodiment, the abovementioned magnetic field coil generates alternating magnetic forces by means of the application of an alternating voltage to said magnetic field coil. Preferably, the alternating voltage is generated by an oscillator.

The term "alternating magnetic forces" as used hereinabove and hereinbelow refers to magnetic forces that are cyclic nature such that the direction in which said forces are exerted is reversed in a periodic manner.

In a further preferred embodiment, the magnetic field coil of the therapeutic system generates direct magnetic forces by means of the application of a direct voltage to said magnetic field coil.

Although the therapeutic system disclosed hereinabove may be used to treat fractures in any part of the body, according to a preferred embodiment the fracture to be treated is located in a limb bone, and the magnetic field coil surrounds said limb.

The present invention also encompasses a method for promoting the healing of bone fractures comprising the steps of:
A. reaming the medullary cavity of each of the fractured bone ends to accommodate a two-part telescopic device, wherein said device comprises a first section more or less telescoped within a second section, wherein said second section contains an internal space, and wherein at least one of said sections is formed of a ferromagnetic material;

B. inserting said second section into the reamed medullary cavity of one bone end and securing it thereto, such that the external opening of said internal space faces towards the other bone end;

C. inserting one end of said first section into the internal space of said second section;

D. inserting the other end of said first section into the reamed medullary cavity of the other bone end and securing it thereto;

E. applying magnetic forces to the ferromagnetic section(s), such that said section(s) is or are caused to oscillate axially with respect to the other section.

Preferably, the magnetic force has a value in the range of 1 to 1000 newtons.

In one preferred embodiment of the method of the invention, the magnetic forces are alternating magnetic forces that are generated by means of an alternating voltage applied to a magnetic field coil located adjacent to the telescopic device.

In another preferred embodiment, the magnetic forces are unidirectional forces that are applied by means of a direct voltage applied to a magnetic field coil located adjacent to the telescopic device, and wherein a spring located within the internal space of the second section of said device provides a counter force to said unidirectional magnetic forces.

In another preferred embodiment, the method further comprises the step of monitoring the position of the device of the invention by use of an imaging technique. In one preferred embodiment, the imaging technique is ultrasonic imaging. In another preferred embodiment, the imaging technique is based on the use of a magnetic sensor.

The method disclosed hereinabove may be used to treat many different types of fracture. In one preferred embodiment, the fracture to be treated is a long-bone fracture. In a more preferred embodiment, the long-bone fracture is a non-union fracture.

In a further aspect, the present invention also encompasses the use of the two-part telescopic device disclosed hereinabove for the primary treatment of long bone fractures.

All the above and other characteristics and advantages of the present invention will be further understood from the following illustrative and non-limitative examples of preferred embodiments thereof.

DETAILED DESCRIPTION OF PREFERRED EMBODIMENTS

Figure 1:
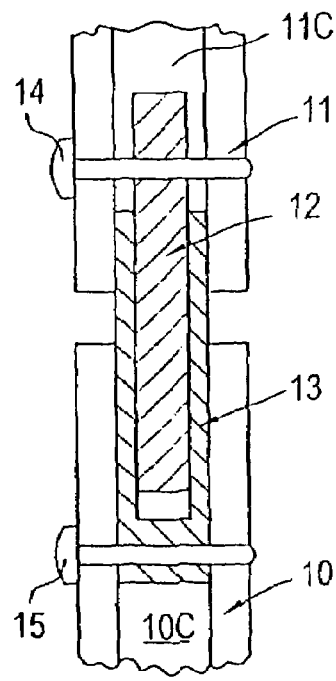
FIG. 1 schematically illustrates the basic structure of the two-part device of the invention, in which the telescopic sections of the device are anchored in complementary sections of fractured or severed bone ends.

The device, as disclosed hereinabove, consists essentially of two sections: a core-like first section, and a socket-like second section, said first section being capable of sliding in and out of said second section in at, essentially telescopic manner. (For ease of description, the "first section" and "second section" of the device, as disclosed hereinabove and claimed hereinbelow, are referred to in the following description of preferred embodiments as "core section" and "socket section" (or readily-identifiable variants thereof) respectively.) It will also be recalled that at least one of these two sections comprises a ferromagnetic material. It is to be noted that the ferromagnetic section(s) may be the core section, the socket section or both sections. In a preferred embodiment, however, both sections of the device are ferromagnetic.

The term "ferromagnetic material" as used herein, refers to magnetic materials having a magnetic constant $K_m$ that varies with an applied electric field, but that is typically much larger than unity. Such materials (which generally are based on one of the five elements: Fe, Co, Ni, Gd or Dy) are characterized by strong interactions between adjacent atomic dipoles, such that even in the absence of an applied magnetic field, there may be spontaneous dipole alignment. (In cases wherein spontaneous dipole alignment occurs, or wherein some ordered dipole alignment remains after removing an external field, the material may be considered to be "magnetic" as well as "ferromagnetic".) In any event, on application of an external field, the ordering or alignment of the dipoles is greatly enhanced, thus generating a large magnetic field.

As disclosed hereinabove, the telescopic device of the invention is intended to be used in conjunction with an externally applied magnetic field, the purpose of said magnetic field being to induce axial movement of one or more of the sections of said device. The magnetic field is preferably generated by means of a solenoid or field coil consisting of a copper winding enclosed within a plastic cover. The internal diameter of the solenoid is designed to appropriately match the external dimensions of the body part to be treated, and is generally in the range of 20 to 30 cm. The length of the solenoid is typically about 10% to 30% greater than that of the telescopic device. The number of turns in the winding, per centimeter length along the solenoid, is adjusted such that an AT (ampere-turn) value in the range of 20,000 to 40,000 may be reached upon using suitable power supplies.

Preferably, the solenoid is provided in a modular form, to allow an easy insertion thereof over the treated body part.

Optionally, the solenoid is coupled with means for removing the heat produced thereby during operation. The heat removal may be accomplished by a water-containing spiral like structure, said spiral being in contact with the solenoid, or by causing air to flow between the turns of the solenoid.

The solenoid may be constructed of any suitable ferromagnetic metals, but is preferably constructed of one of one or more of the following materials: iron, stainless 430, PH174.

The device of the invention may be used in the following two essentially different ways, in accordance with the desired clinical effect:

a) Essentially unidirectional movement of the ferromagnetic section(s), for use in situations where the desired clinical effect is an increase or decrease in bone length.

b) Bidirectional movement of the ferromagnetic section(s), for use in situations where the clinician wishes to promote and assist the healing of bone fractures.

A. Unidirectional Mode

The Basic Implant Structure: A telescopic orthopedic device in accordance with the invention, as shown schematically in FIG. 1, is adapted to lengthen a skeletal bone such as a leg or arm bone. To prepare the bone for lengthening, it is necessary for an orthopedic surgeon to perform an osteotomy in which the bone is severed to create complementary sections 10 and 11. The degree to which these bone sections are forced to separate by an implant anchored in the sections ultimately determines the extent to which the bone has been lengthened.

And to prepare the bone for installation of the implant, it is possible for the surgeon before or after severing the bone to ream a canal through the marrow of the bone so that bone section 10 is then provided with an intramedullary cavity 10c and bone section 11 with an intramedullary cavity 11c.

The implant includes a ferromagnetic magnet section 12 in the form of a core telescoped within a tubular non-magnetic section 13. Magnetic section 12 of the implant is received within cavity 11c of bone section 11 of the severed bone and is secured thereto by a screw 14 or other fastener means. The non-magnetic section 13 is received in cavity 10c of bone section 10 and is secured thereto by a screw 15. Hence the respective implant sections are anchored in the complementary bone sections.

In practice, the core section 12 of the implant, instead of being cylindrical may have an elliptical cross section so that it cannot be rotated within socket section 13 which has a like cross section. But the core can be axially displaced so that it can be advanced axially to lengthen the implant. Alternatively, the cross section could be a circle having a flat segment, again for the purpose of preventing rotation but not axial movement. One is able for the same purpose to provide other core and socket section shapes.

Core section 12 is preferably fabricated by a "hard" ferromagnetic material which is polarized to form a permanent magnet having a North Pole at one end and a South Pole at the opposite end. A suitable metallic material for core 12 is Alnico or other alloy having a high coercive force so that even though the core is small it acts as a powerful permanent magnet. Alternatively, a non-metallic "hard" ferromagnetic material such as a ceramic ferrite may be used for the core. The advantage of using a ferrite to fabricate core section 12 rather than a metal which must be machined to assume the corrugated formation of the core, is that a ferrite can easily be molded to assume the desired configuration.

It is not essential to the invention that the magnetic core section 12 of the implant be composed entirely of "hard" permanent magnet material, but only that it include a sufficient amount of such material as to be able to react to an impulse of magnetic force to effect a positive stepping action.

Thus core section 12 may be constituted by a hollow cylinder of "hard" ferromagnetic material filled with a non-magnetic synthetic plastic composition. Or core section 12 may be formed by a solid plug of non-magnetic material having a head or cap of hard magnetic material functioning as a permanent magnet.

The socket section 13 of the implant may, in one embodiment, be made entirely of non-magnetic plastic or metal material. A preferred material for this purpose is one commonly employed in prosthetic implants, such as titanium or a steel alloy. Or socket 13 may be molded of high-strength synthetic plastic material such as polypropylene or polyethylene. It is essential that the material from which the implant is composed be biologically compatible with the tissue in which it is embedded. In another embodiment, socket section 13 may comprise a ferromagnetic material, such as one of the ferromagnetic materials listed hereinabove.

When the implant is installed so that its socket section is held within cavity 10c of bone section 10 and its core section is held within cavity 11c of bone section 11, the implant then bridges the separated complementary bone section.

The implant can be pre-constructed so that both components are integrated and placed in either a retrograde or antegrade fashion into the medullary canal under fluoroscopic guidance. In the course of a stepwise bone lengthening procedure, the length of the bridge is incrementally increased until the overall length of the severed bone attains a predetermined value. Typically, the incremental length may be from 2 to 20 centimeters.

To allow adequate time for the severed bone sections to knit together and heal and to permit the soft tissues surrounding the bone to adjust thereto in the course of the incremental bone-lengthening procedure, there should be a time interval between successive lengthening steps of sufficient duration for this purpose, such as at least one day per step.

It is necessary that the implant, in the course of a lengthening procedure, maintain the bone sections bridged thereby in a proper alignment so that when the severed bone is healed, it is properly formed and not crooked. Because the implant is formed by a core telescoped in a socket and is coaxial therewith, the linearity of the implant is maintained as it is being lengthened.

Figure 2:
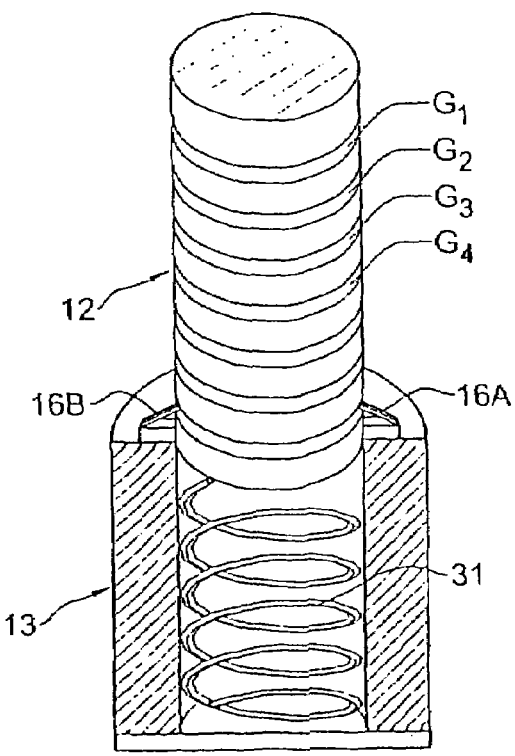
FIG. 2 shows a preferred embodiment of the device which is intended for use in altering bone length.

The circumferential surface of core section 12 of the implant, as shown in FIG. 2 is corrugated to form a series of equi-spaced annular grooves G1, G2, G3 etc. which define ratchet teeth. These teeth are detented by a pair of pawls 16A and 16B mounted at diametrically opposed positions on the upper end of socket section 13, the pawls falling into successive grooves when the core is being pulled out of the socket in which it is telescoped. The pawls are preferably in the form of flat metal springs having tongues that fit into the grooves, the spring flexing when the core is advanced so that the pawls can then snap into the next groove.

Figure 3:
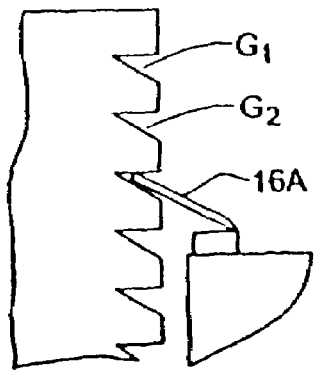
FIG. 3 is a detail of the ratchet mechanism included in the implant shown in FIG. 2.

The grooves G1 etc. along core 12 have a triangular cross section which as best seen in FIG. 3 is defined by a horizontal upper wall and an angled lower wall inclined downwardly with respect to the upper wall. Hence when the tongue of the flat spring is within a groove and one then seeks to displace the core downwardly, this movement is arrested by the horizontal wall of the groove which then abuts the tongue. But when one seeks to displace the core upwardly, the tongue then slides down the inclined wall of the groove to permit this advance.

Hence the pawl and ratchet teeth mechanism associated with the core and socket make it possible to jack up the implant bridging the bone sections of the bone to be lengthened incrementally in a stepwise manner to progressively increase the length of the bridge until the overall length of the severed bone attains its predetermined desired value.

In the implant shown in FIG. 2, the means which prevents the core from advancing backwards into the socket and thereby reducing the length of the bridge are the detents which engage the ratchet teeth. To resist retrograde movement in the implant arrangement shown in FIG. 2, one may to this end place underlying the core section 12 a helical spring 31 which urges the core upwardly and therefore resists downward movement of the core into the socket. The spring therefore acts to maintain the core at its advanced position.

Other known means may be included in the implant to permit the required axial movement in one direction and to prevent retrograde movement.

Second Embodiment

The invention does not require cylindrical or tubular implant sections but only that the first section telescope into the second section regardless of their cross sectional geometry. What is essential to the invention is that the first section functions as a permanent magnet and that the second section be non-magnetic so that when the implant installed in the complementary sections of the severed bone is subjected to an impulse of magnetic force, this will induce the first section to incrementally lengthen the implant and thereby lengthen by one step the severed bone.

Figure 4:
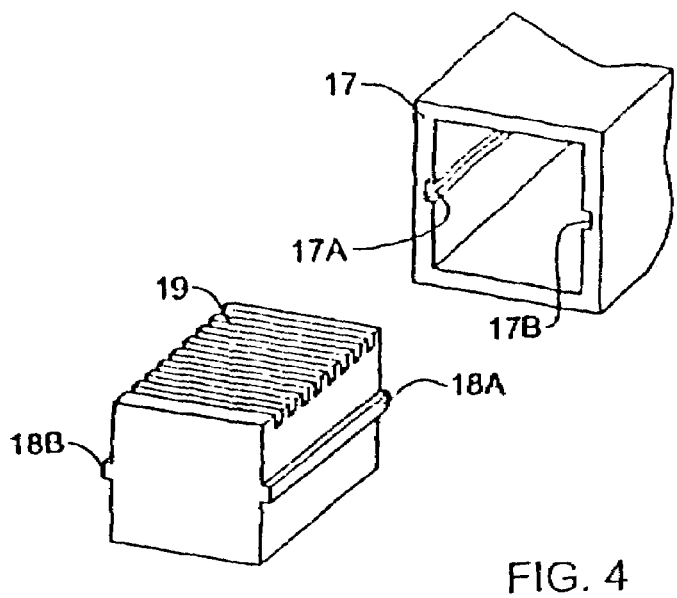
FIG. 4 shows another embodiment of the device.

Thus the implant shown in FIG. 4 includes a non-magnetic section 17 which is channel-shaped and therefore has a rectangular cross section. Formed in the parallel sidewalls of this section are longitudinally extending grooves 17A and 17B.

Telescopically received in section 17 is a magnetic core section 18 having a square cross section that matches the cross sectional area between the sidewalls of section 17. Ribs 18A and 18B formed on opposing sides of section 18 slide into grooves 17A and 17B of the walls.

Thus the magnetic cross section 18 can more or less telescope within the non-magnetic section 17. The top wall of section 18 is provided with a row of transverse grooves defining ratcheted teeth 19 which cooperate with a pawl or detent (not shown) to limit the advance of this section to one step per impulse, as in the embodiment shown in FIG. 2.

Advance of the Implant

An implant, in accordance with the invention, must be capable of being advanced incrementally. But it may also be made capable, when at any one ratcheted step, of causing the core of the implant to vibrate in order to promote the bone-healing process.

The core ratchet can be designed so that its operation is limited to incremental advances or so that it can also vibrate at each step. A core whose operation is to be limited to incremental steps, may be provided with annular grooves G1, G2, G3 etc. as shown in FIG. 2 having an optimal height in the range of 0.1 to 1.5 millimeters. A core which can also vibrate at each step without causing it to advance to the next step is then provided with grooves of greater height in the range of 0.15 to 0.4 mm, thereby giving the pawl more freedom.

Figure 5:
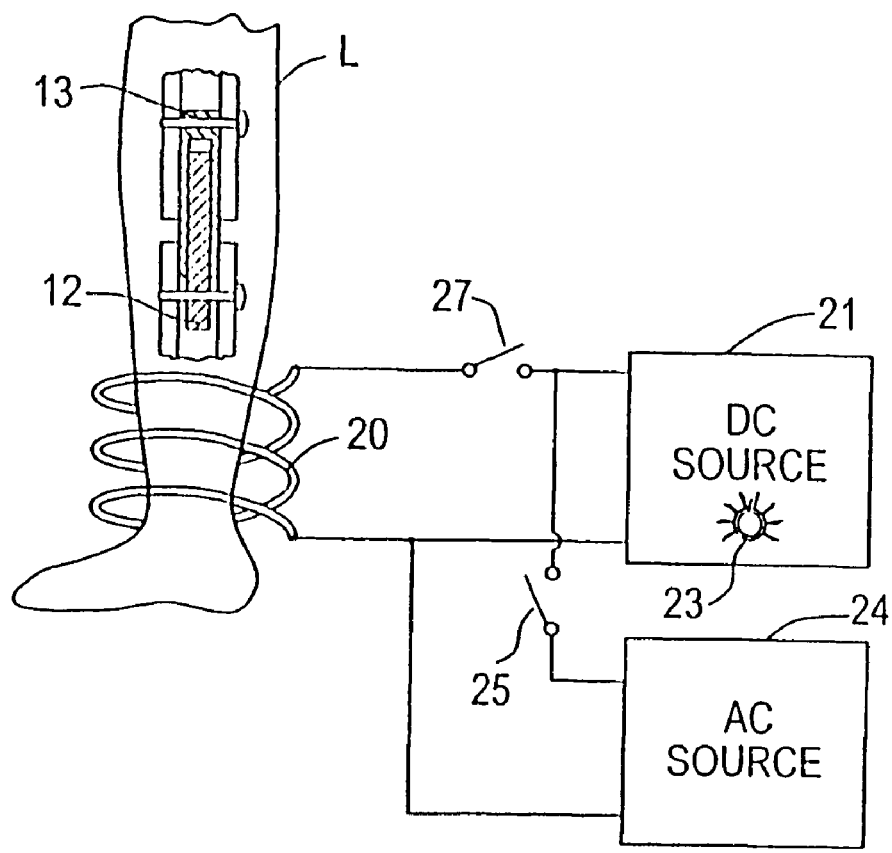
FIG. 5 illustrates the system by which an implant installed in a severed leg bone is magnetically actuated in order to generate either unidirectional or bidirectional, oscillatory, movement of the ferromagnetic section(s) of the telescopic device.

Incremental advance of the permanent magnet core section 12 is effected by means external to leg L which as shown in FIG. 5 has the implant 12–13 installed between the complementary bone sections of the severed bone to be lengthened and healed.

These external means are constituted by a magnetic field coil 20 surrounding leg L adjacent to the region of the implant therein and a DC power source 21 connected to the coil through a control switch 27. Source 21 is provided with a voltage control potentiometer 23 so that the strength of the field may be raised or lowered to a required degree.

Each time switch 27 is momentarily closed, as surge of current flows unidirectionally through coil 20 to produce an electromagnetic field whose lines of flux penetrate the leg and are intercepted by magnet core section 12 of the implant. The direction of current flow in the coil is such as to produce a magnetic field whose polarity repels the polarized core and hence acts as an impulse of magnetic force to advance the core of one step.

The implant, which functions dynamically, behaves like a dynamic loudspeaker. In a speaker of this type, a field coil mounted on a cone is displaced axially with respect to a fixed permanent magnet, the displacement of the coil being in accordance with variations in current flowing through the coil. In a dynamic implant in accordance with the invention, the coil is at a fixed position whereas the permanent magnet core anchored in a bone section is movable and is displaced to an extent and in a direction in accordance with variations in current flowing through the coil.

When one wishes to vibrate the core at each step before the core is advanced to the next step, then coil 20 is connected to an A–C generator 24 through a switch 25. When switch 25 is closed, the resultant A–C electromagnetic field causes the core to oscillate. The frequency of oscillation is such as to promote the healing process.

Ideally, coil 20 comprises helical windings that encircle the appendage enclosing the bone to be lengthened such the when the coil is energized momentarily, the resultant surge or impulse of magnetic force is applied in the axial direction to maximize the pull exerted by the impulse on the magnetic section of the implant. And instead of a helical coil, a ring-shaped toroidal coil may be designed so as to slip over the appendage.

When the location of the bone to be lengthened is such that it cannot be surrounded by a magnetic field coil, then use may be made of a pair of planar or pancake coils which flan opposing sides of the bone location and are connected in series to a power source to produce combined magnetic fields which exert an axial force on the implant.

As a practical matter, it is difficult in each bone lengthening procedure to predetermine the magnitude of the magnetic force impulse necessary to cause the implant to advance a single step per implant and no more. Clearly an excessive force may cause the core section of the implant to jump several steps, whereas a weak force may be insufficient to cause this section to advance even one step.

The magnitude of the magnetic force impulse appropriate to a given implant installation is best determined empirically by means of a voltage supply for the field coil having a control potentiometer. The potentiometer is operated to slowly raise the voltage applied to the coil until a point is reached where a stepping action takes place, as indicated by the clicking sound of the ratchet mechanism. This clicking sound can best be heard by means of a stethoscope. Having determined the magnitude of voltage that brings about a stepping action, the same magnitude is applied in successive steps.

Healing:

The healing process by which the bone sections knit together in the course of a bone-lengthening procedure can be promoted by discharging into the gap region between the bone section in which healing transpires a growth factor, such as a bone morphogenetic protein or a decalcified bone matrix in granular or paste form. Other growth factors are useable, such as transforming growth factor beta or osteogenic growth peptide or OP-1.

Figure 6:
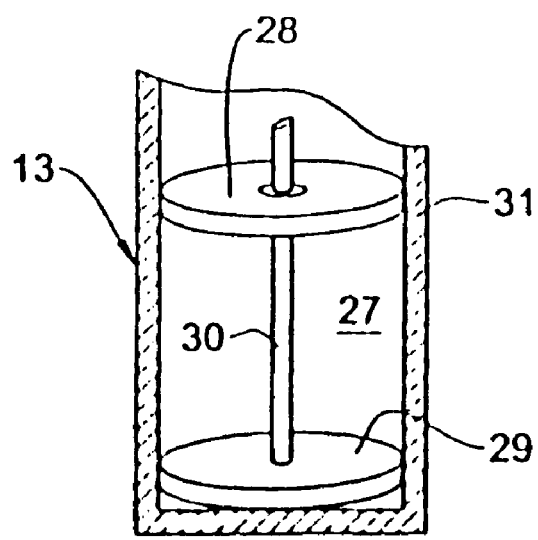
FIG. 6 shows an implant in whose socket section is a reservoir containing a healing agent which is discharged into the gap region between the severed sections of the bone.

To this end, in the embodiment of the implant shown in FIG. 6 socket 13 includes at its base a well or reservoir filled with a growth factor borne by a carrier to create a gel 27, the well being confined by a disc 28. At the bottom of this well and slideable thereon is a piston 29 operated by a piston rod 30 attached to core section 12 telescoped in socket 13. Hence each time the core section is advanced, the piston is then raised thereby to apply a pressure pulse to the growth factor gel, causing it to extrude into the gap region between the bone sections through orifices 31 in the wall of socket section 13 of the implant.

Instead of a growth factor, the gel or cream may be an antibiotic such as penicillin or cephalosporin, or any other suitable antibiotic to reduce the risk of infection in the course of the healing process, or to treat bone infected in the course of being lengthened.

Also useful for healing is a sub-dermal reservoir adapted to cause infusion into the bone lengthening area of mesenchymal cells. This is of particular value when treating the limbs of a cancer patient who has been exposed to irradiation giving rise to a lack of mesenchymal cells.

Imaging:

When in a bone lengthening procedure an external adjustable frame is used which is mechanically coupled to an internal implant, then one observing the frame can determine, by means of a scale on the frame, the extent to which the bone has been lengthened.

But in a bone lengthening procedure in accordance with the Invention in which there is no mechanical linkage between an internal implant and an external frame, one is unable to tell the extent to which the bone has been lengthened, if indeed it has been lengthened at all. Thus while one knows the degree to which the implant is lengthened, per step, one cannot be sure that with each application of a magnetic force, the core has actually stepped, particularly since the resistance offered by the leg to each step in a bone lengthening procedure often varies from step to step.

Should one depend on hearing a clicking sound to determine how many steps the implant has advanced incrementally, one must be careful to correctly count the clicks. Yet one cannot be sure that with each click, there has been an actual stepwise advance.

Figure 7:
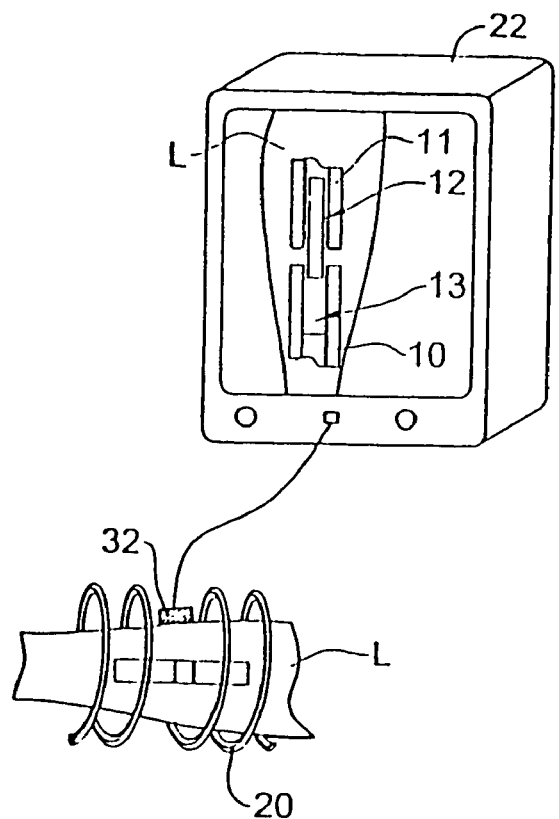
FIG. 7 shows an ultrasound imaging system on whose screen is displayed the bone being lengthened by the implant.

In order therefore to be able to actually see the operation of the implant and the extent to which it is lengthening the bone, use may be made of an ultrasound imaging system, as shown in FIG. 7. The piezoelectric transducer 32 of this system generates periodic ultrasonic pulses that are propagated through the leg tissue and are reflected by the bone. This transducer is placed on leg L at a position overlying the implant therein. Coil 20 surrounding the leg is configured to create an opening therein to accommodate the transducer, so that the transducer operates in the region of the magnetic field emanating from the coil.

One therefore sees on the monitor screen 22 of the ultrasound imaging system, a full scale image of the implant (12–13) interposed between the bone sections (10–11). And one can measure on the screen the adjusted distance between the severed sections of the bone. As an alternative to the use of an ultrasound imaging technique, the present invention also makes provision for imaging techniques based on the use of magnetic sensors.

In a procedure in accordance with the invention the proximity of coil 20 to the implant depends on the dimensions of the appendage and the locations of the implant therein. Hence the power required to produce a magnetic force sufficiently strong to step the core depends on how close the coil is to the core and the strength of the magnet. But with imaging, one can see whether the magnetic force acting on the core does in fact step the core, and if it does not, one can then increase the power applied to the coil to bring about the desired action.

This imaging system is a useful adjunct to the implant procedure but not a prerequisite thereto. Other systems such as an oscilloscope connected to a microphone can be used to detect the click sound generated by advancement of the ratchet mechanism. Also X-ray imaging can be used to visualize lengthening of the implant. However, this entails multiple exposures to ionizing radiation and may have adverse side effects.

The implant functions not only to lengthen (or shorten) the bone, but also when the bone is lengthened (or shortened) and healed, to reinforce the bone. The dimensions of the implant must be appropriate to those of the bone in which it is implanted. Hence a bone which has a large cross sectional area and when severed offers a relatively high resistance to being lengthened, demands an implant whose dimensions are appropriate to the bone. The same implant may be unsuitable for a bone having a smaller cross sectional area.

A preferred material for forming the non-magnetic section of the implant is titanium. The reason for the use of titanium rather than any other material is that it is known from the use of titanium in a dental implant in which a titanium post is screwed into a hole drilled in a jaw bone, that the bone then literally proceeds to fuse with the titanium. Such fusion does not take place with other materials.

Third Embodiment

Instead of using the implant to lengthen a bone, it can be adapted to shorten a bone to a desired extent. To this end, a short piece of bone to be shortened is excised to provide a relatively large gap between the ends of the complementary bone sections. The ferromagnetic core section of the implant is then lodged in one of these bone sections and the non-magnetic socket section in which the core is telescoped is lodged in the other bone section.

Then by applying an external magnetic force thereto, the core section of the implant is caused to advance an incremental step further into the socket section, thereby reducing the gap between the bone sections. This action is repeated until the shortened distance between the ends of the bone section provides a bone of the desired shortened length.

When the implant is adapted to shorten a bone, the detenting of the core section must be such as to permit its stepwise advance into the socket section and prevent retrograde movement.

Fourth Embodiment

An orthopedic implant adapted to transport a bone fragment requires a ferromagnetic core the opposite ends of which are telescoped within respective non-magnetic sockets. These sockets are lodged in the complementary ends of the severed bone sections.

When a magnetic force is applied to the implant, the core is then advanced to step further into one socket and at the same time to step further out of the other socket without changing the length of the bone, for the distance between the ends of the complementary bone section remains unchanged.

In this way, a bone fragment may be transported from one bone section to the other in a direction that depends on the polarity of the magnetic force applied to the core.

While there have been disclosed preferred embodiments of the invention, it is to be understood that many changes may be made therein without departing from the spirit of the invention. Thus the implant may be used not to lengthen a bone but as a splint to maintain a fractured bone in proper alignment as the bone undergoes a natural healing process. In this situation, a canal is reamed through the marrow of the fractured bone to receive the implant. One section of the implant is anchored in a section of the bone on one side of the fractured region, and the other section is anchored in the bone section on the opposite side of this region. In this case the implant is not magnetically actuated unless in order to straighten out the fractured bone it is necessary to lengthen the implant.

B. Bidirectional (Oscillatory) Mode

In the case of a long-bone fracture, the core section is preferably attached to the distal section of the fractured bone, the socket section being fixed into the cavity of the proximal part of the fracture. The present invention, however, also encompassed the possibility of the reverse situation, that is, wherein the core section is fixed to the proximal bone segment, while the socket section is attached to the distal segment.

In many cases, it will be highly advantageous to install the device of the invention such that the core section is inserted deep inside the socket section. In such cases, one end of each of the two sections of the device will be fixed into the medullary cavity of one of the bone segments, while the other, free, extremity of each section will extend into the medullary cavity of the other segment (without being attached thereto). The free end of the core section, in such cases, will not be in direct contact with living tissue within the medullary cavity, but rather enclosed within the inner space of the socket section.

In other cases, rather less overlap between the two sections will be required, with only one of the sections (either the socket section or the core section) having both of its extremities situated within the bounds of the medullary cavities of both of the fractured bone segments. In still other cases, the overlap will be minimal, the region of insertion of the core section into the socket section being confined to the space between the fractured bone segments.

A preferred embodiment of a two-part telescopic device for use in promoting the healing of bone fractures in accordance with the present invention is shown schematically in FIG. 1. In this figure, the two sections of a fractured long bone are represented by numerals 10 and 11. By way of preparation before installing the device of the invention, the surgeon may ream a canal through the bone marrow of each of the fractured bone ends to from intramedullary cavities 10C and 11C.

The embodiment of the two-part device depicted in FIG. 1 includes a ferromagnetic section 12 in the form of a core telescoped within a tubular non-magnetic section 13. Said ferromagnetic section 12 of the device is received within cavity 11C of bone section 11 of the fractured bone, and is secured thereto by means of one or more locking screws 14 or by the use of any other suitable bio-compatible fastener means. Non-magnetic section 13 in inserted into cavity 10C of bone section 10 and is secured thereto by means of one or more locking screws 15. In one embodiment of the invention, said locking screws 14 and 15 are each inserted into, and anchored within, the bone cortex on one side of the medullary cavity. In a more preferred embodiment, said locking screws are inserted into, and anchored within, the bone cortex on both sides of the medullary cavity. It may thus be seen that the two sections of the device of the invention are anchored in the medullary cavities of the two fractured bone ends.

Core section 12 is preferably fabricated of a "hard" ferromagnetic magnetic material which is polarized to form a permanent magnet having a North Pole at one end and a South Pole at the opposite end. A suitable metallic material for core 12 is Alnico or any other alloy having a high coercive force so that even though the core is small, it acts as a powerful permanent magnet. Alternatively, a non-metallic "hard" ferromagnetic material such as a ceramic ferrite may be used for the core. The advantage of using a ferrite to fabricate core section 12 rather than a metal which must be machined to assume the corrugate formation of the core is that a ferrite can easily be molded to assume the desired configuration.

It is not essential to the invention that the magnetic core section 12 of the device be composed entirely of a "hard" permanent material, but only that it include a sufficient amount of such a material as to be able to react to an impulse of magnetic force to effect the desired electromechanical oscillation of the device.

The non-magnetic socket section 13 of the device may be made entirely of a non-magnetic plastic or metal material. A preferred material for this purpose is one commonly employed in prosthetic implants, such as titanium or a steel alloy. The reason for the preferred use of titanium is that it is known from the use of this material in dental implants in which a titanium post is screwed into a hole drilled into a jaw bone, that the bone then literally proceeds to fuse with the titanium. Such fusion does not appear to take place with other materials.

Preferably, the magnetic core section 12 is fitted with a small projection (not shown in the figures) on its external surface, in close proximity to its free end. This projection engages a longitudinal slot in a corresponding portion of the socket section 13, the end of said slot that is closest to the free end of said socket section forming a stop, beyond which the projection on core section 12 cannot travel. The purpose of this arrangement is to prevent said magnetic core section 12 from moving outwards from socket section 13 further than a preset value, or from completely separating therefrom. In one preferred embodiment, the abovementioned projection has a triangular, fin-like, outline shape.

When the device is installed such that its magnetic section is held within cavity 10C of fractured bone section 10 and its non-magnetic section is held within cavity 11C of bone section 11, these two sections of said device then bridge the fractured and separated bone sections. Thus, in addition to the use of the device (in conjunction with the externally-placed magnetic field as disclosed hereinabove and described hereinbelow), the two-part device of the invention may be used as a static stabilizing device for use in the very first stages of the management of fractured bones. A further advantage of the device of the invention is that its use from the earliest stage of hospital management through to complete healing ensures that the fractured sections are maintained in their correct alignment, in view of the co-axial, rigid nature of said device. Yet another advantage offered by the device of the invention is that it may be used in place of an earlier-inserted intramedullary nail, without the need for further preparation of the fractured bone segments.

In order for the apparatus of the invention to function optimally, both as an oscillatory two-part device and as a static bridging device, it is necessary to construct said apparatus such that its dimensions are appropriate to those of the bone in which it will be installed. Thus, a bone which has a large cross-sectional area requires a device having dimensions appropriate for said bone. The same device, however, may be unsuitable for a bone having a smaller cross-sectional area.

The device of the invention may be pre-joined so that the integrated device is placed in either a retrograde or antegrade manner into the medullary canal under fluoroscopic guidance.

Figure 8:
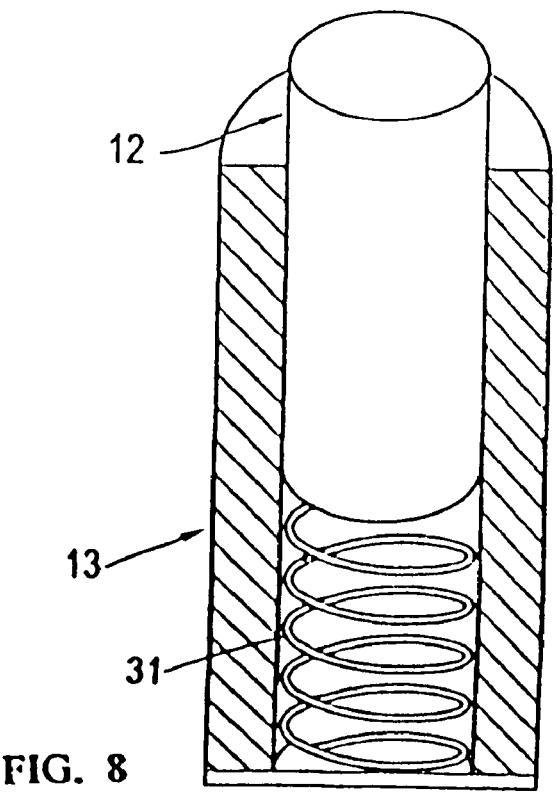
FIG. 8 depicts one preferred embodiment of the device intended for use in promoting the healing of fractures, in which a helical spring is used in order to generate counter force to unidirectional magnetic forces.

Although the device of the invention may be constructed with a circular cross-sectional shape, as shown in FIG. 8, any other cross-sectional form that permits the magnetic and non-magnetic sections to oscillate freely in relation to each other may be used. Such cross-sectional forms include but are not limited to square, rectangular, square or rectangular with rounded corners or elliptical or ellipsoid.

In one preferred embodiment of the invention, the core section 12 and the socket section 13 are caused to oscillate in relation to each other by the application of an external magnetic field. The range of movement of one of said sections in relation to said other section is 10 μm to 2 mm, with a periodicity of oscillation of 0.1–1000 Hz. Thus, in the case of the embodiment illustrated in FIG. 1, said external magnetic field is an alternating field, such that alternating magnetic forces are applied to ferromagnetic core section 12. Said core section then moves in and out of socket section 13 in a way essentially similar to the motion of a piston within a cylinder of an internal combustion engine. The use of the device of the invention together with an external magnetic coil is depicted in FIG. 5. The external means for applying the magnetic field shown in this figure comprise a magnetic field coil 20 surrounding the affected limb L in the region adjacent to the location of the installed device, said coil being placed such that its entire structure is placed distal to the distal extremity of the magnetic core section 12. In the case of the embodiment presently described, an alternating magnetic field is applied by connecting coil 20 to an alternating current (AC) generator 24 through a switch 25. When switch 25 is closed, the resultant AC electromagnetic field causes the ferromagnetic core section 12 to oscillate within socket section 13, as described hereinabove. Preferably the AC voltage used to generate the AC electromagnetic field is between 1 and 1000 V, with a frequency of between 0.1 and 1000 Hz.

In another preferred embodiment of the device, as shown in FIG. 8, a helical spring 31 may be fitted beneath the core section 12 in the internal space of socket section 13. Said helical spring may be attached to either the end of core section 12, the base of the internal space of socket section 13, to both of these structures. The purpose of spring 31 is to provide counter force to a unidirectional magnetic force which, in FIG. 8, is applied in a direction such that ferromagnetic core 12 moves further inside socket section 13. It should be noted that although the embodiment depicted in FIG. 8 shows the use of a helical spring, any other suitable type of spring device may be used in its place. In this embodiment of the invention, the unidirectional magnetic force is effected by means of a direct current (DC) power source, as shown in FIG. 5. Said DC power source is fitted with a voltage control potentiometer 23 so that the strength of the field may be raised or lowered to the required value. Preferably, the DC voltage is in the range of 1–1000 V. Each Lime switch 27 is closed, a surge of current flows unidirectionally through coil 20 to produce an electromagnetic field whose lines of flux penetrate the leg and intercepted by magnet core section 12 of the device. The direction of current flow in the coil is such as to produce a magnetic field whose polarity is such that said core section is impelled towards the base of the internal space of core section 13. As a consequence of this reduction of space within the internal cavity of socket section 13, helical spring 31 (FIG. 8) is compressed. When the potential energy of said spring reaches a critical value (corresponding to the point wherein the kinetic energy of the spring is at its lowest value, and its potential energy at its highest value), said spring is able to overcome the path of travel of core 12 and pushes said core in the opposite direction, and in so doing, allows the spring 31 to relax, until said core reaches a stop position that is defined by the furthest point of travel of the above-described projection on the surface of said core within the slot present in socket section 13. This process then proceeds in a cyclical manner, thus causing core 12 to oscillate within socket section 13.

In an alternative preferred embodiment, the spring and the magnetic coil are arranged such that the unidirectional magnetic forces cause the ferromagnetic core section 12 to travel outwards, away from the base of socket section 13, thus extending the total effective length of the device. In this case, the helical spring reaches its maximal extended state, wherein the potential energy stored therein reaches a maximal value, said potential energy serving to counter the unidirectional magnetic forces and to drive the core section 12 back towards the base of socket section 13.

It is to be noted that although the field coil 20 depicted in FIG. 5 is a helical coil, other suitable coils, such as ring-shaped toroidal coils that may be readily slipped over the appendage to be treated, may also be used. When the location of the fracture to be treated is such that it cannot be surrounded by a magnetic field coil, use may be made of a pair of planar or pancake coils which flank opposite sides of the bone location, and which are connected in series to a power source to produce combined magnetic fields which exert an axial force on the device of the invention.

Without wishing to be bound by any theory, it is believed that it is the oscillation of the two fractured bone sections into which the oscillating two-part device is attached, which is responsible for the promotion of the healing process.

The device of the invention may be used to assist healing of bone fractures by application of the electromagnetic field as described above, thus causing the ferromagnetic section to oscillate within the other, non-magnetic section. Preferably, the device is caused to oscillate for periods of between one minute and 120 minutes, up to three times per day. Alternatively, the device may be used in a continuous treatment regime.

The healing process by which fractured bone sections knit together can be accelerated and assisted by use of the apparatus and method of the present invention as described hereinabove. This healing process may be further assisted by discharging into the gap region between the fractured bone ends a healing factor, such as a growth factor with healing properties such as bone morphogenetic protein or a decalcified bone matrix In granular or paste form. Other growth factors may also be used, including (but not limited to) transforming growth factor beta and osteogenic growth peptide (OP-1). Although these growth factors have been in clinical use for many years, the device of the present invention permits their controlled, local, high-concentration release into the region of the healing fracture.

To this end, the device of the invention may incorporate a well or reservoir filled with a growth factor within the base of socket section 13. Said growth factor may be borne by a carrier to create a gel, the well being confined by a disc. In one preferred embodiment, a piston arrangement (not illustrated) attached to core section 12 is used to apply a pressure pulse to the growth factor preparation within its well. Hence, each time the core section is advanced, the piston is raised thereby applying a pressure pulse to the growth factor gel, causing it to extrude into the gap region between the bone sections through orifices in the wall of socket section 13 of the device.

Instead of a growth factor, the gel or cream may comprise an antibiotic such as penicillin or cephalosporin, or any other suitable antibiotic to reduce the risk of infection in the course of the healing process. An additional benefit of the use of a locally-released antibiotic in conjunction with the device of the present invention is that it will permit the wider use of said device, particularly in cases of fracture associated with more severe soft tissue damage (such as Gustilo classes IIIA and IIIB), might be more successfully treated by intramedullary devices.

In one preferred embodiment, the antibiotic may be contained within a well or reservoir and delivered by use of a mechanical piston system that is linked to ferromagnetic core section 12 (as described hereinabove). Alternatively, according to another preferred embodiment, the external surfaces of the core section 12 and the socket section 13 may be coated with antibiotic-containing granules. Such a coating will serve as a slow-release system, allowing delivery of the antibiotic both to the region of the fracture (thus speeding the healing process) and to the inside of the device of the invention (thus preventing problems of bacterial contamination thereof).

Also useful for healing is a sub-dermal reservoir adapted to cause infusion of mesenchymal cells into the healing bone region.

The abovementioned healing factors, growth factors and antibiotics may be released from the device of the invention in various amounts, in either a continuous or controlled manner. In the case of continuous release, the device of the invention may be loaded with between 1 and 10 g of the aforementioned healing factors, growth factors and antibiotics. In the case of controlled release, the device may be loaded with up to 1 mg of these substances. These doses are given for the purpose of exemplification only, and are not intended to limit the amounts of such substances that may be used in combination with device of the present invention.

While specific embodiments of the invention have been described for the purpose of illustration, it will be understood that the invention may be carried out in practice by skilled persons with many modifications, variations and adaptations, without departing from its spirit or exceeding the scope of the claims.

The invention claimed is:

1. A two-part telescopic intramedullary orthopedic device capable of connecting two adjacent fractured or severed bone ends, characterized in that said device comprises
a first section capable of being inserted into the medullary cavity of one of the fractured or severed bone ends, and secured thereto, and
a second section capable of being inserted into the medullary cavity of the other fractured or severed bone end and secured thereto,
wherein said second section comprises an internal space communicating with an external opening, and wherein said first section is more or less telescoped within said internal space of said second section, and
wherein one of said sections comprises a ferromagnetic material and the other section is either constructed entirely of a non-magnetic material or comprises a ferromagnetic material, wherein the ferromagnetic section(s) are actuable by an external magnetic field applied in a substantially axial direction, such that one section may be caused to move axially in relation to the other section, and wherein said axial movement may be either bidirectional or essentially unidirectional.

2. The device according to claim 1, wherein the ferromagnetic material is a hard ferromagnetic material.

3. The device according to claim 2, wherein the hard ferromagnetic material is Alnico.

4. The device according to claim 2 wherein the hard ferromagnetic material is a ferrite.

5. The device according to claim 1, wherein the non-magnetic material is a synthetic plastic material.

6. The device according to claim 1, wherein the non-magnetic material is titanium.

7. The device according to claim 1, wherein the first section of said device is formed by a core of ferromagnetic material, and the second implant section is formed by a tubular socket into which the first section is telescoped.

8. The device according to claim 1, wherein the first section has a non-circular cross section and the internal space of the second section has a corresponding cross section whereby said first section cannot be rotated within said second section.

9. The device according to claim 8, wherein telescopic advancement of the first section within the second section by incremental steps is achieved by a series of annular grooves formed along the first section, said grooves defining ratchet teeth that are detented by a pawl mounted on the second section.

10. The device according to claim 9, wherein the pawl is a flat spring having a tongue extending into a groove in the series thereof.

11. The device according to claim 10, wherein a pair of pawls is mounted on opposite sides of the second section.

12. The device according to claim 11, wherein the grooves have a triangular cross section and a groove height which permits the first section ratcheted by the pawl to vibrate.

13. The device according to claim 1, in which the second implant section includes a reservoir loaded with a flowable healing agent and provided with an orifice from which is emitted a charge of the agent each time the first implant section is advanced an incremental step.

14. The device according to claim 13, further comprising means to subject the agent in the reservoir to a pressure pulse each time the first implant section is advanced to force the agent out of the orifice.

15. The device according to claim 14, wherein the healing agent is a growth factor which promotes a bone healing process.

16. The device according to claim 15, wherein the healing agent is an antibiotic substance.

17. The device according to claim 1, wherein the first section has a square cross section and the second section which is channel-shaped includes parallel sidewalls banking a cross section area matching the cross section of the first section whereby the first section can be telescopically received in the second section.

18. The device according to claim 17, wherein the first section has a top wall that is notched to define ratchet teeth that are detented by a pawl mounted on the second section whereby the first section can be incrementally advanced beyond the second section.

19. An orthopedic implant assembly adapted to manipulate the length of a skeletal bone to attain a predetermined length in a procedure in which a canal may be reamed through the bone to accommodate so implant and the bone severed to define complementary bone sections each having a cavity therein to receive a respective section of the implant, said assembly comprising:

A. a device according to claim 1, and
B. means external to said device to apply magnetic forces in a substantially axial direction thereto to cause the one or more ferromagnetic sections of said device to shift progressively in one direction with respect to the other section of said device to change the separation therebetween until the severed bone attains said predetermined length.

20. The assembly according to claim 19, wherein the magnetic forces are constituted by successive impulses each of which causes the first section to advance an incremental step.

21. The assembly according to claim 20, wherein the impulses of magnetic force are produced by applying direct current power pulses to a magnetic field coil adjacent to the bone to be lengthened or shortened.

22. The assembly according to claim 21, wherein the bone to be manipulated is embedded in a body appendage and the field coil surrounds the appendage.

23. The assembly according to claim 19, further including means to apply an alternating magnetic force to the device after the first section of said device has been incrementally advanced to cause said first section to vibrate to promote the healing process.

24. The assembly according to claim 23, wherein the alternating magnetic force is produced by a field coil adjacent to the device to which an alternating voltage is applied.

25. The assembly according to claim 24, wherein the alternating voltage is generated by an oscillator whose frequency is such as to promote the healing process.

26. The device according to claim 1, further comprising mechanical means for reversing the direction of the axial movement of the ferromagnetic section(s), in order to allow bidirectional axial movement of said section(s).

27. The device according to claim 26, wherein the mechanical means comprise a spring located in the internal space of the second section, such that said spring is positioned between the base of said internal space and the free end of the first section.

28. The device according to claim 27, wherein the one or more ferromagnetic sections are at least partially formed by a hard ferromagnetic material.

29. The device according to claim 28, wherein the hard ferromagnetic material is Alnico.

30. The device according to claim 28, wherein the hard ferromagnetic material is a ferrite.

31. The device according to claim 27, wherein the non-magnetic section is formed by a synthetic plastic material.

32. The device according to claim 27, wherein the non-magnetic section is formed of titanium.

33. The device according to claim 27, wherein the second section includes a reservoir loaded with a flowable healing agent and provided with an orifice from which is emitted a charge of said agent.

34. The device according to claim 33, further comprising means to subject the agent in the reservoir to a pressure pulse.

35. The device according to claim 33, wherein the healing agent is a growth factor which promotes bone healing.

36. The device according to claim 33, wherein the healing agent is a antibiotic agent.

37. The device according to claim 27, wherein the device is configured for the primary treatment of long bone fractures.

38. Therapeutic system for promoting the healing of bone fractures comprising a device according to claim 1 together with means external to said device for applying magnetic forces in a substantially axial direction thereto.

39. Therapeutic system according to claim 38, wherein the means for applying magnetic forces comprises a magnetic field coil situated adjacent to the telescopic device.

40. Therapeutic system according to claim 39, wherein the magnetic field coil generates alternating magnetic forces by means of the application of an alternating voltage to said magnetic field coil.

41. Therapeutic system according to claim 40, wherein the alternating voltage is generated by an oscillator.

42. Therapeutic system according to claim 38, wherein the magnetic field coil generates direct magnetic forces by means of the application of a direct voltage to said magnetic field coil.

43. Therapeutic system according claim 38, wherein the fracture to be treated is located in a limb bone, and wherein the magnetic field coil surrounds said limb.

44. A method of lengthening or shortening a skeletal bone to attain a predetermined length comprising the steps of:

A. reaming the marrow of the bone to be lengthened or shortened to create a canal to accommodate a two-part telescopic intramedullary orthopedic device having a first section more or less telescoped within a second section, wherein one of said sections comprises a ferromagnetic material and the other section is either constructed of a non-magnetic material or comprises a ferromagnetic material;
B. severing the bone to define complementary bone sections, each having a cavity therein;
C. inserting the first section of the device into the cavity in one section of the bone and securing it thereto;
D. inserting the second section of the device into the cavity of the other bone section and securing it thereto, whereby the degree to which the hone sections are separated and the severed bone is lengthened or shortened depends on the extent to which the first section projects beyond the second section; and
E. applying successive magnetic force impulses to the first section in a substantially axial direction to cause it to advance an incremental step per impulse until the severed bone has attained said predetermined length.

45. The method according to claim 44, wherein successive incremental steps in the advance of the first section are separated by time intervals of sufficient duration to permit effective healing of the severed bone.

46. The method according to claim 45, wherein the duration of each interval lasts at least a full day.

47. The method according to claim 44, further comprising the step of monitoring the change of length of the implant by ultrasonic imaging.

48. The method according to claim 44, wherein the parameters of the magnetic force lie in the range of 100 to 1000 newtons.

49. The method according to claim 44, wherein the implant is advanced in increments of 0.1 to 1 mm per day.

50. Method for promoting the healing of bone fractures comprising the steps of:

A. reaming the medullary cavity of each of the fractured bone ends to accommodate a two-part telescopic device, wherein said device comprises a first section more or less telescoped within a second section, wherein said second section contains an internal space, and wherein at least one of said sections is formed of a ferromagnetic material;
B. inserting said second section into the reamed medullary cavity of one bone end and securing it thereto, such that the external opening of said internal space faces towards the other bone end;
C. inserting one end of said first section into the internal space of said second section;
D. inserting the other end of said first section into the reamed medullary cavity of the other bone end and securing it thereto;
E. applying magnetic forces in a substantially axial direction to the ferromagnetic section(s), such that said section(s) is or are caused to oscillate axially with respect to the other section.

51. Method according to claim 50, wherein the magnetic force has a value in the range of 1 to 1000 newtons.

52. Method according of claim 50, wherein the magnetic forces are alternating magnetic forces generated by means of an alternating voltage applied to a magnetic field coil located adjacent to the telescopic device.

53. Method according to claim 50, wherein the magnetic forces are unidirectional forces that are applied by means of a direct voltage applied to a magnetic field coil located adjacent to the telescopic device, and wherein a spring located within the internal space of the second section of said device provides a counter force to said unidirectional magnetic forces.

54. Method according to claim 50, wherein the fracture to be treated is a non-union fracture.

55. Method according to claim 54, wherein the non-union fracture is a non-union fracture of a long bone.

* * * * *